United States Patent [19]

Fenster et al.

[11] Patent Number: 4,595,949
[45] Date of Patent: Jun. 17, 1986

[54] SYSTEMS AND METHODS FOR TRANSLATING RADIATION INTENSITY INTO PIXEL VALUES

[76] Inventors: Paul Fenster; Zvi Netter; Yair Shimoni, all of c/o Elscint Ltd., P.O. Box 5258, Haifa, Israel

[21] Appl. No.: 614,839

[22] Filed: May 29, 1984

[30] Foreign Application Priority Data

Jul. 26, 1983 [IL] Israel ............................................ 69326

[51] Int. Cl.$^4$ .......................... H05G 1/64; H05G 1/32; H05G 1/50; H04N 5/32
[52] U.S. Cl. ...................................... 358/111; 378/99; 378/108; 378/110; 378/112
[58] Field of Search .................. 378/99, 100, 108–112, 378/97; 358/110–112

[56] References Cited

U.S. PATENT DOCUMENTS

| | | | |
|---|---|---|---|
| 3,567,854 | 3/1971 | Tschantz et al. | 378/99 |
| 3,911,273 | 10/1975 | Franke | 378/97 |
| 4,061,920 | 12/1977 | Mollendorf et al. | 378/99 |
| 4,423,521 | 12/1983 | Haendle et al. | 378/108 |
| 4,473,843 | 9/1984 | Bishop et al. | 378/99 |
| 4,486,896 | 12/1984 | Richter et al. | 378/110 |

Primary Examiner—Craig E. Church
Assistant Examiner—Charles F. Wieland
Attorney, Agent, or Firm—Sandler & Greenblum

[57] ABSTRACT

Improved diagnostic imaging methods and systems for automatically controlling variable parameters used when translating detected radiation intensities caused by radiation that has passed through an object and impinged on a detector to fixed values for display images by determining the maximum and minimum intensities at the impinged on detector locations and adjusting the parameters as functions of the said maximum and minimum intensities.

48 Claims, 2 Drawing Figures

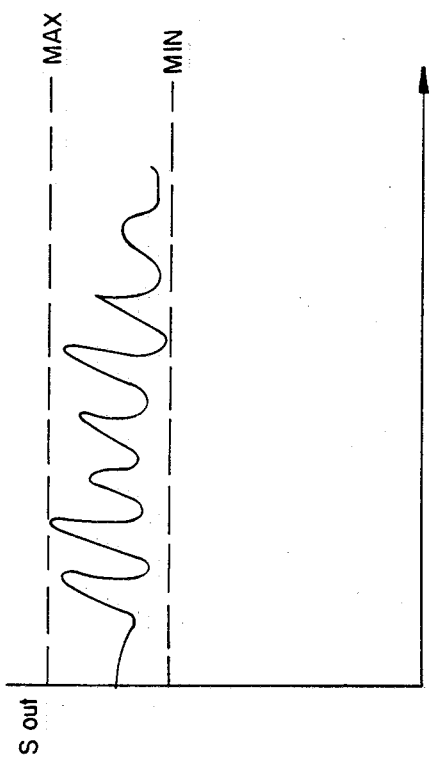

SYSTEMS AND METHODS FOR TRANSLATING RADIATION INTENSITY INTO PIXEL VALUES

FIELD OF THE INVENTION

This invention is concerned with diagnostic imaging devices and more particularly with digital fluorography (DF) systems and methods for automatically optimally varying parameters used in changing detected radiation intensity to pixel values.

BACKGROUND OF THE INVENTION

In diagnostic imaging systems, it is desirable to maximize resolution, signal to noise ratio and the relative intensity contrast between different materials through which the radiation passes, i.e. bone, soft tissue, contrast material, gas, etc. Scientists in the field are continuously attempting to improve resolution, lower the noise and increase the contrast to improve the quality of the pictures obtained.

In digital fluorography, the person conducting the study generally learns by experience where to set the various controls on the system. For example, if the person conducting the study wants to image an object that has small changes in relative opaqueness then, the voltage output of the X-ray power supply is set high to provide the requisite photon energy level. Other controls generally are available to the clinician. For example, controls are available for changing the X-ray tube current, when the power supply provides energy in a continuous mode. If energy is supplied in a pulsed mode then the length of the pulse or the number of pulses used per image can be varied. Also, the number of optical photons is controlled by varying the iris or the shutter opening in the optical system. Other functions of DF signals such as those described in the patent application entitled "Improved Digital Fluorography", bearing Ser. No. 546177, filed, in the United States on Oct. 27, 1983, now U.S. Pat. No. 4,555,728, which is assigned to the assignee of this application are controlled by the analog-to-digital converter circuitry.

A problem with these imaging systems is that a variation in one of the parameters has an effect on at least certain of the other parameters. Thus when one parameter is set to a desired value the adjustment of another parameter will change the first adjusted parameter. Accordingly, there is a real need for a system that automatically adjusts at least certain of the parameters necessary to obtain high quality images.

BRIEF DESCRIPTION OF THE INVENTION

According to a broad aspect of the invention a DF system is provided wherein at least certain adjustable parameters are automatically adjusted to provide high resolution images with minimal noise and optimal contrast, said system comprising:
a source of penetrating radiation,
detector means for detecting radiation emanating from said source and converting the intensity (the total energy of photons impinging on a unit area) of said detected radiation as a function of location, to output signals, said output signals having a "one to one" relationship with said detected radiation intensity,
means for determining the maximum and minimum intensities detected, and
means for using said determined maximum and minimum detected intensities for adjusting said parameters.

A "one to one" relationship is used here in the mathematical sense to mean that for every intensity value there is a unique output signal value and for each output signal value there is a unique intensity value. Such functions are alternatively referred to as "single-single valued" functions. The use of a one to one relationship enables interchanging the terms intensities and output signal values.

According to a feature of the invention the system is first calibrated to set certain parameters; then, the system parameters are adjusted to obtain an output that is a function of the maximum and the minimum output.

BRIEF DESCRIPTION OF THE DRAWINGS

The above mentioned and other features and objects of the invention will be best understood in the context of the following description of preferred embodiments of the invention taken in conjunction with the following drawings, in which:

FIG. 2 is a graphic representation of a typical output signal vs. time response curve of a DF system at the output of a video camera.

GENERAL DESCRIPTION

Figure 1:
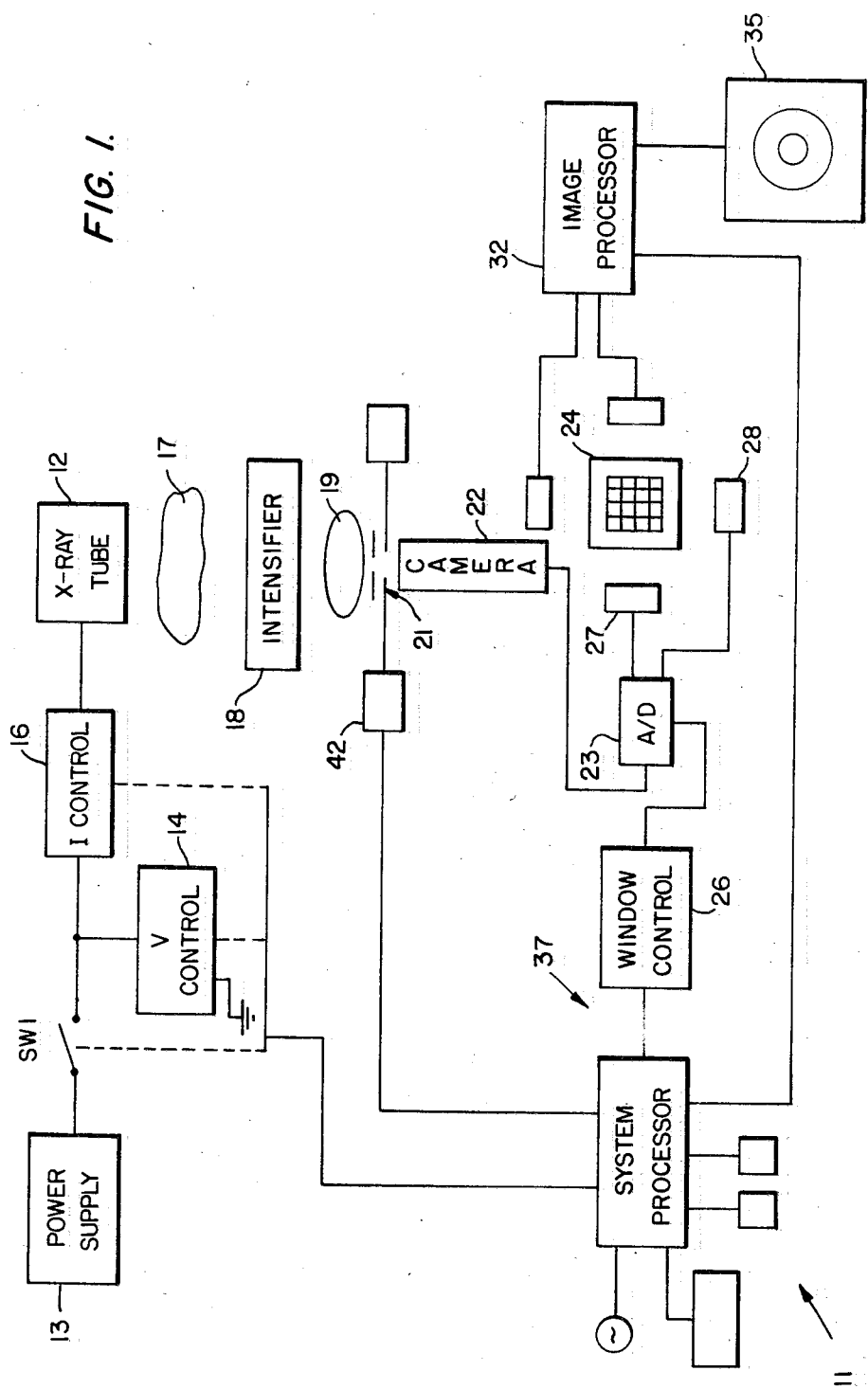
FIG. 1 shows in block diagram form an arrangement for automatically setting certain parameters in digital fluorography systems.

The digital fluorography system 11 of FIG. 1 includes a radiation source, such as X-ray tube 12. The tube 12 is energized by power supply 13 which operates either in a continuous mode or a pulsed mode.

The output of the power supply 13 is coupled through switch SW1 to voltage control means, indicated at 14. The voltage control means is shown connected between switch SW1 and ground. A current control means 16 is serially connected between the switch SW1 and the input to X-ray source 12. The voltage and current are separately controlled by controls 14 and 16. It should be understood that any current and voltage control system known in the art can be employed.

The radiation output of X-ray tube 12 is directed through an object such as a patient 17, or anything simulating a patient wherein a portion of the radiation is absorbed. The absorption attenuated radiation is converted to light and intensified by means such as intensifier tube 18. The face of tube 18 is divided into pixels so that the light variations are specifically located on the face of the tube. The light variations are transmitted through the optical system, comprising a lens arrangement 19 and a shutter arrangement 21, to a video camera 22.

The output of the video camera is a video signal including intensifier pixel location information. The video signal is connected to an analog-to-digital converter 23 which converts and processes the camera's video signals to digital signals. More particularly, the digital signals are on-loaded into a matrix arrangement indicated by matrix 24. Each coordinate location of the matrix corresponds to a pixel location on the image intensifier. The value of the digital signal at the matrix location is a function of the intensity of the radiation that impinged on the detector surface in the said corresponding location.

Digital fluoroscopic systems in use presently generally employ video cameras with a 1000:1 signal to noise ratio (SNR). These cameras have linear responses to light intensities for output signals ranging from zero to 1 volt. Experience has taught that it is best to calibrate the camera so that radiation intensity of 1 milliroentgen at the image intensifier is converted to an output signal of 1 volt. However these values may differ for other types of cameras and accordingly the term "brightest radiation" is used herein instead of 1 milliroentgen and the term "maximum video signal amplitude" is used instead of 1 volt. The above noted linear response is a specific and preferred case of the previously discussed one to one relationship.

If the signal is linear with respect to the integral absorbing power of the material in the line of sight, rather than with respect to the light intensity, then the signal varies, depending on the object, over a range of about twenty five percent of the maximum signal amplitude, as shown in FIG. 2. Thus the video signal varies between say 600 to 900 MV or 750 to 950 MV. There are similar variations both in the lower and higher voltage levels depending on the object, among other things.

The above linear response is one type of monotonic response functions. The advantage of using monotonic response functions is, among other things, that the maximum and minimum output signals are obtained for maximum and minimum intensities. The advantages of a linear function include a uniform sensitivity over the entire range and the ease of mathematical transformation. Therefore, the maximum values and the minimal values, such as shown in FIG. 2, are readily translated into intensity values. Accordingly, the preferred embodiment uses a linear response function although the invention is in no way limited to such functions.

Means are provided to cause the analog to digital converter to operate on the range of changes in the signals rather than on the total range of signals from zero to the maximum value. More particularly in the described embodiment variable window control means 26 are provided which is set to pass only the varying portion of the signal. The window enables the selection of a top and a bottom threshold. The window control means is effective for limiting the output signal which is being converted to image data to only those values which are consistent with the range over which the intensity varies.

The digital output of the converter 23 is on-loaded at particular coordinate locations in the matrix as the digital output is supplied to the matrix 24 through x,y locator devices 27 and 28, respectively. Groups of matrices represented by matrix 24, are used for storage prior to further processing the data by means 32 which operates on the data in a manner customary in digital fluorographic systems to prepare the data for display as images on device 35.

The system 11 is shown to be under the control of processor arrangement 37. The processor may control the voltage amplitude of the pulse in the pulse mode or the voltage amplitude of the power supply in the continuous mode. It may also control the X-ray tube current including the pulse length in the pulse mode. The shutter or iris 21 is controlled by processor 37 through control system indicated by block 42. A window control 26 that controls the operation of converter 23 is also controlled by the processor 37.

In operation the system controls at least the following parameters, which are functions of the maximum and minimum intensities at the image intensifier surface:

(a) Photon energy—the X-ray tube voltage determines the maximum photon energy. Changes in the photon energy change the relative intensity contrast between different materials traversed by the X-rays because different materials have different absorption spectra. In angiography, the average photon energy is set at the beginning of the examination to be somewhat higher than the K absorption edge of iodine. Experienced users usually set the X-ray tube voltage at somewhere between 60 and 100 KV, approximately, depending on the thickness of the object being imaged.

(b) Number of photons—with the X-ray tube voltage maintained constant, the charge passing through the X-ray tube (usually measured in milliampere seconds) determines the number of photons. This parameter affects the quantum noise and the patient dosage. If the number of photons is too high the dose is too high but the quantum noise is low. When the number of photons is low the dosage is decreased but the noise is increased.

Ideally, the nunber of photons is set so that the quantum noise will affect the least significant bit of the acquired data but only the least significant bit. This serves to limit the patient dosage and to keep the quantum noise as the major noise component.

For "continuous" systems the charge passing through the X-ray tube is controlled by the tube current. For "pulsed" systems it is controlled by the pulse width, tube current and repetition number. For these systems the current is usually set to maximum, to enable operation with the shortest pulse width and lowest pulse repetition number possible. For most purposes one pulse per image is preferred. The term "current specifications" is used herein to cover all possibilities. The number of photons times the average photon energy equals the energy output of the source, and is proportional to the charge passing through the X-ray tube.

(c) Number of optical photons per X-ray quantum detected by the camera—affects the maximum video signal (the level of the video signal at the brightest radiation; i.e. the highest intensity available). In the illustrated system this parameter is controlled by the shutter 21. The number of photons hitting the T.V. camera should be such that the brightest point of interest on the screen gives 1 V out of the T.V. camera. Then, although the number of optical photons is increased, the signal to noise ratio caused by the X-Ray photons is unchanged. However the overall SNR is improved since the noise of the T.V. camera is practically constant over the range of the signals used.

Thus for a particular dose requirement (i.e. X-Ray photon noise requirement) the optimum iris position is that which causes the brightest spot of interest to give a 1 V video signal.

The number of optical photons per X-ray quantum should be changed (i.e. by changing the iris) in only two cases:

(i) the X-ray generator has reached its power output limit; or (ii) the X-ray generator power output can be changed only in gross steps (for example by a factor of 2) and a smaller change is wanted (say 20% or a quarter of a shutter stop)

(d) and (e) The two thresholds, i.e. the upper and the lower thresholds of the analog to digital converter 23, are set so the maximum voltage is translated to the highest digital output and the lowest voltage in the range of varying voltages is translated to a pre-determined digital output-usually just high enough to ensure that all possible signals will be translated to positive digital values.

There exist in the art ADC's wherein one can set the upper threshold and the gain—i.e. the range of voltages which is converted to the full digital range. Thus in a preferred embodiment setting of the threshold parameters as a function of the range of the varying voltages minimizes digitization noise and maximizes the number of levels of useful information in the image.

All of the above parameters, except for the photon energy (X-ray tube voltage) are set automatically by the inventive system.

The procedure, according to a broad aspect of the invention, comprises:

I. Signal level optimizing (SLO); and
II. Further ADC setting (FAS)

The SLO step should be done at least each time the system is turned on, and preferably before each study.

With an ADC setting that translates the maximum video signal amplitude to a fixed digital output value (say, 128), a test shot is acquired with a patient or with a phantom representing a patient, and the average value over a portion of the "brightest radiation" region in the image is compared with the above fixed value. The test shot is acquired with the zoom lens, image intensifier and voltage selected for the intended study.

The results of the comparison are automatically translated by the central processor to provide new current or pulse length or pulse number settings (depending on the X-ray generator) and if necessary (again, automatically) to a new iris setting to assure that the "brightest radiation" part of the image corresponds to a maximum video signal amplitude. The new iris setting may be automatically implemented. The test shot can be repeated if desired to recheck that the average value of the "brightest radiation" region is indeed the fixed value.

The FAS step is done with voltage, current, iris and pulse length all set to either the values obtained in the SLO step or some accepted value for the type of study.

A test shot is acquired with the patient in the desired position and the ADC set to as wide a range as possible (that is, with the gain as small as possible). A region of interest (ROI) in the image is selected. This ROI is assumed to contain the whole range of intensities, with the highest intensity not to be changed during the actual examination. Thus, the top threshold can be automatically set so that the highest intensity input to the ADC produces the highest digital output of the ADC. The actual relationships between input video voltages and output digital values depend on the actual ADC used, but are linear for digital fluorography quality ADCs.

The gain, however, should not be set to fit the actual range of intensities measured, as the injection of contrast material will reduce the minimum intensity. A pre-fixed range is added, therefore, to the actually measured range of intensities, by setting the lowest ADC threshold at a voltage such that for the actually measured minimum intensity the ADC yields a digital output of a fixed value, greater than zero by the amount (approximately) that the contrast material will reduce the intensity. The range is translated to a gain setting, again with a linear equation depending on the actual ADC used as well as other gains in the system used. The equations for calculating the ADC settings depend also on the iris setting. The fixed positive digital value (or the added range) depends on the clinical procedure used (for example, the amount of iodine injected into the patient) and may be changed accordingly. For example, for inter arterial injections values around 60 are recommended, while for intravenous injections lower values are acceptable. The user can,, here too, repeat the test shot to be assured of the procedure's validity.

A synergistic benefit of the described system and method is that the window of the analog to digital convertor is readily adjusted to fit the range between the actual maximum and minimum intensity values rather than servicing the intensity range between zero and the maximum value as is done in the prior art. This adjustable window enables more efficient use of the ADC and memories, among other things.

In operation the DF system is calibrated with a patient or a phantom which provides a range of radiation absorptions extending from, and including, the maximum opacity and the minimum opacity of a representative patient. For example, a step wedge phantom may be used to accomplish the SLO step. The source voltage is set for each particular study. In angiography the voltage is set so that the average photon energy is higher than the K absorption edge of iodine. The tube voltage is set to approximately 60 KV for thin objects, such as a hand, and to approximately 100 KV for thick ones, such as the abdomen of an obese patient. An ADC setting that translates the maximum video signal to a fixed value, such as 128, is used to acquire a test image.

During the test shot the detected radiation is converted to electrical signals containing location information (analog video signals). The locations correspond to the place that the radiation impinges on the detector. The analog signals are converted to digital signals and placed into matrix locations that correspond to the detector locations of the particular signals, and thus can be displayed as an image—the test image.

The average value of the "brightest radiation" region is obtained and compared to the said fixed value. The ratio of the two values is used to calculate the new setting for the current amplitude or pulse length or number of pulses and if necessary the shutter or iris setting.

The ADC settings are adjusted to the correct values to fit each patient. The settings vary as a function of the weight (and density) of the patient. A test image is acquired with the ADC initially set with its upper threshold at its maximum value to allow for as high video signals as possible and the gain as small as possible to allow for as wide a range of intensities as possible. No contrast material is injected for the test shot. The source is energized with the settings as determined in the calibration proceedings, or with arbitrary settings based on experience, but always with the same settings as are to be used during the intended study.

A region of the interest (ROI) in the test image is selected that is assumed to include the entire range of intensities. The maximum and minimum digital values in the ROI are found and are used to calculate the new upper threshold and the new gain such that the brightest radiation will be translated to approximately the highest digital value and the lowest intensity to a predetermined low digital value.

This low digital value is selected to allow for a decrease in intensities as contrast material is injected to the patient. The highest intensity does not change appreciably during the study. The new ADC settings are automatically implemented. The equipment is now ready for the study.

The linear equations used in the preferred embodiment of the invention are as follows:

| | |
|---|---|
| New Upper Threshold = | A1(Max Value) + B1(Min Value) + C1 |
| New Gain = | A2(Max Value) + B2(Min Value) + C2 |
| New Current specifications* = | A3(Max Value) + C3 |
| New Iris* = | A4(Max Value) + B4(new current) + C4 |

*The new current specification setting is a recommendation only. The actual setting of a new current depends on the step size at which said current can be changed and on whether the maximum current has been reached. Alternatively the new pulse lengthor repetition number are changed provided the maximum length or repetition number are not exceeded. The constants A4, B4 and C4 are changed depending on whether or not a new current parameter is used and what is the new current parameter. The constants A1, B1, C1, A2, B2, C2 may depend on the exact iris setting. The new parameters are changed automatically to therby optimize the ADC usage and the translation of detected radiation to digital pixel values in the displayed image. The systems's full use of the ADC range among other things reduces digitalization noise.

The constants A1-A4, B1-B4, C1-C4 are based on the characteristics of the system components. They are measured during system installation and stored in the system's memory to be changed only after changes, modifications or recalibrations are performed on the system.

It should be understood that while the term digital fluorography is used herein, the systems disclosed apply also to related systems including digital radiography and the like.

While the invention has been described with reference to particular embodiments, it should be understood that the description is made by way of example and not as a limitation on the scope of the claimed invention. For example, while the window control 26 is shown separate from the converter 23, it may be an integral part of the converter or separate therefrom within the scope of the invention. In addition it is contemplated that the window may control the upper and lower thresholds or the upper threshold and the gain.

What is claimed is:

1. A diagnostic imaging method for automatically substantially simultaneously controlling a plurality of variable parameters governing the translation of detected radiation intensity to pixel values for video display images, said method comprising the steps of:
   energizing a source of penetrating radiation to transmit the radiation through an object,
   detecting on detector means the radiation that has passed through the object,
   measuring the energy intensity of said radiation at each location on the detector means,
   determining the maximum and minimum values of said measured intensities, and
   using said determined maximum and minimum intensities for adjusting said plurality of variable parameters.

2. The method of claim 1 wherein said radiation detecting step includes the steps of:
   detecting at the detector means the locations of the energy intensity caused by photons impinging on said detector locations,
   converting said energy intensities into signals containing information about the intensities at each location, said signals being linear with respect to the integral absorbing power of the object on the radiation passing through the object in the path from the source to the detector, and
   converting said signals into digital signals.

3. The method of claim 2 wherein said signals comprise analog signals changing in time so that each instant in time corresponds to a unique location on the detector.

4. The method of claim 3 wherein said converting of said intensities to said analog signals include the following steps:
   intensifying the image formed by the detector, creating an intensified image on a "target" plate
   scanning said "target" plate with a video camera, and producing a video signal.

5. The method of claim 4 wherein the step of converting said analog signals to said digital signals is done by an Analog to Digital converter (ADC) with variable threshold and gain.

6. The method of claim 2 including the step of converting the radiation that has passed through the object to light signals, and converting said light signals into analog signals.

7. The method of claim 2 where the plurality of variable parameters include:
   the top threshold of the signal converted to a digital signal.

8. The method of claim 1 where the plurality of variable parameters include:
   the total energy of the radiation used for each image.

9. The method of claim 2 where the plurality of variable parameters include:
   the range of intensities of the radiation converted to positive digital signals.

10. The method of claim 3 where the plurality of variable parameters include:
    the intensity level converted to the maximum analog signal.

11. The method of claim 4 where the plurality of variable parameters include:
    the intensity level converted to the maximum video signal.

12. The method of claim 5 where the plurality of variable parameters include:
    the upper threshold of said ADC which controls the level of video signal converted to the maximum digital signal.

13. The method of claim 4 where the variable parameters include:
    the range of video signals converted to the full range of digital signals.

14. The method of claim 1 wherein said determining step includes the steps of:
    storing said digital signals into matrix locations, said locations corresponding to the locations on the detector impinged by photons, and scanning said matrix locations todetermine the minimum and maximum values of said stored digital signals.

15. The method of claim 14 including:
    performing preparatory test operations for setting at least certain of said plurality of variable parameters prior to the actual patient study.

16. The method of claim 15 where one of the said preparatory operations comprises:
    setting the energy output of said source to obtain a maximum analog signal.

17. A method of claim 15 wherein one of said preparatory operations comprises setting the complete available range of digital values to cover only the range between the maximum and minimum intensity values.

18. The method of claim 16 where said setting of the energy output comprises the steps of:
   energizing the source with predetermined ADC settings, first current specifications and a first iris size,
   comparing the resulting highest video signals with the maximum video signals, and
   adjusting the first current specifications to obtain new current specifications and the first iris size to obtain a new iris size so the resulting highest video signal will equal the maximum video signal.

19. The method of claim 18 including the step of calculating the new current specifcations using linear equations, as a function of the measured highest digital signal and the digital signal corresponding to the maximum video signal.

20. The method of claim 19 including the step of calculating the new iris size using a linear equation in which the new iris size is a function of the digital signal corresponding to the maximum video signal and the new current specifications.

21. The method of claim 17 wherein the step of using the determined maximum and minimum values comprises the steps of:
   determining a digital range of signals defined by the minimum and maximum intensity values, and
   using the determined digital range to set the ADC so that it will convert to the full digital range only analog video signals resulting from intensities in a wanted range.

22. The method of claim 21 including the step of calculating the new ADC setting, using linear equations, as a function of said maximum and minimum digital values.

23. The method of claim 14 and controlling the changes in the variable parameters using the maximum and minimum values by calculating the parameters as linear functions of the maximum and minimum values, and setting the parameters to the calculated values.

24. A diagnostic system for automatically substantially simultaneously controlling a plurality of variable parameters governing the translation of detected radiation intensity to pixel values for display images, said system comprising:
   means for energizing a source of penetrating radiation to transmit the radiation through an object,
   means for detecting on detector means the radiation that has passed through the object and measuring the energy intensity at each location on the detector means,
   means for determining the maximum and minimum values of said measured intensity, and
   means for using said determined maximum and minimum intensities for adjusting said plurality of variable parameters.

25. The system of claim 24 wherein said detecting means includes:
   means for detecting at the detector the locations of the energy intensity caused by photons impinging on said detector locations,
   means for converting said energy intensities into signals containing information about the intensities at each location, said signals being linear with respect to the integral absorbing power of the object on the radiation passing through the object in the path from the source to the detector, and
   means for converting said signals into digital signals.

26. The system of claim 25 wherein said signals comprise analog signals changing in time so that each instant in time corresponds to a unique location on the detector.

27. The system of claim 26 wherein said means for converting of said intensities to said analog signals include:
   means for intensifying the image formed by the detector,
   means for creating an intensified image on a "target" plate, and,
   means for scanning said "target" plate with a video camera, and producing a video signal.

28. The system of claim 27 wherein the means for converting said analog signals to said digital signals is done by an analog to digital converter (ADC) with variable threshold and gain.

29. The system of claim 25 including means for converting the radiation that has passed through the object to light signals, and
   converting said light signals into analog signals.

30. The system of claim 25 where the plurality of variable parameters include:
   the top threshold of the signal converted to a digital signal.

31. The system of claim 24 where the plurality of variable parameters include:
   the total energy of the radiation used for each image.

32. The system of claim 25 where the plurality of variable parameters include:
   the range of intensities of the radiation converted to positive digital signals.

33. The system of claim 26 where the plurality of variable parameters include:
   the intensity level converted to the maximum analog signal.

34. The system of claim 27 where the plurality of variable parameters include:
   the intensity level converted to the maximum video signal.

35. The system of claim 28 where the plurality of variable parameters include:
   the upper threshold of the said analog to digital converter which controls the level of video signal converted to the maximum digital signal.

36. The system of claim 27 where the plurality of variable parameters include:
   the range of video signals converted to the full range of digital signals.

37. The system of claim 23 wherein said means for determining includes:
   means for storing said digital signals into matrix locations, said locations corresponding to the locations on the detector impinged by said photons, and
   means for scanning said matrix locations to determine the minimum and maximum values of said stored digital signals.

38. The system of claim 37 including:
   means for performing preparatory test operations for setting of at least certain of said plurality of parameters prior to the actual patient study.

39. The system of claim 38 wherein said means for performing preparatory operations comprises:
   means for setting the energy output of said source to obtain a maximum analog signal.

40. A system of claim 38 wherein means for performing said preparatory operations comprises:
means for setting the complete available range of digital values to cover only the range between the maximum and minimum intensity values.

41. The system of claim 39 where said means for setting of the energy output comprises:
means for energizing the source with predetermined ADC voltage, current specifications and iris size,
means for comparing the resulting highest video signals with the maximum video signals, and
means for adjusting the current specifications and the iris size so the resulting highest video signal will equal the maximum video signal.

42. The system of claim 41 including means for calculating the new current specifications using linear equations, as a function of the measured highest digital signal and the digital signal corresponding to the maximum video signal.

43. The system of claim 41 including means for calculating the new iris size using a linear equation wherein the new iris size is a function of the digital signal corresponding to the maximum video signal and the new current specifications.

44. The system of claim 40 wherein the means for using the determined maximum and minimum values comprises:
means for determining the digital range defined by the minimum and maximum intensity values, and
means for using the determined digital range to set the analog to digital converter so that it will convert to the full digital range only analog video signals resulting from intensities in a wanted range.

45. The system of claim 44 including means for calculating the new ADC setting using linear equations, in which the new ADC setting is a function of said maximum and minimum digital values.

46. The system of claim 37 and means for controlling the changes in the variable parameters using the maximum and minimum values by calculating the parameters as linear functions of the maximum and minimum values, and setting the parameters to the calculated values.

47. The method of claim 19 including the step of calculating the new iris size using a linear equation which is a function of the digital signal corresponding to the maximum video signal and the first current specifications.

48. The method of claim 41 including means for calculating the new iris size using a linear equation which is a function of the digital signal corresponding to the maximum video signal and the first current specifications.

* * * * *